(12) United States Patent
Brekke et al.

(10) Patent No.: US 10,080,940 B2
(45) Date of Patent: *Sep. 25, 2018

(54) SHAFT FITTING SYSTEM

(71) Applicant: SRI SPORTS LIMITED, Kobe-shi, Hyogo (JP)

(72) Inventors: Dustin J. Brekke, Fountain Valley, CA (US); Matthew R. Daraskavich, Huntington Beach, CA (US); Nathaniel J. Radcliffe, Huntington Beach, CA (US)

(73) Assignee: SRI SPORTS LIMITED, Kobe-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/340,424

(22) Filed: Nov. 1, 2016

(65) Prior Publication Data

US 2017/0050094 A1 Feb. 23, 2017

Related U.S. Application Data

(63) Continuation of application No. 14/449,906, filed on Aug. 1, 2014, now abandoned, which is a
(Continued)

(51) Int. Cl.
*A63B 53/10* (2015.01)
*A63B 60/42* (2015.01)
(Continued)

(52) U.S. Cl.
CPC .............. *A63B 60/42* (2015.10); *A63B 53/00* (2013.01); *A63B 53/04* (2013.01); *A63B 53/10* (2013.01);
(Continued)

(58) Field of Classification Search
CPC ......... A63B 53/10; A63B 53/00; A63B 53/04; A63B 71/06; A63B 59/0074;
(Continued)

(56) References Cited

U.S. PATENT DOCUMENTS 3,685,041 A  8/1972  Kondur, Jr.
4,836,545 A  6/1989  Pompa
(Continued)

FOREIGN PATENT DOCUMENTS

JP   S60170740 A   9/1985
JP   H05346382 A   12/1993

OTHER PUBLICATIONS

May 11, 2016 Office Action Issued in U.S. Appl. No. 14/449,906.

*Primary Examiner* — Stephen Blau
(74) *Attorney, Agent, or Firm* — Oliff PLC (57) ABSTRACT

A method of selecting a preferred golf shaft for a player who uses an existing golf shaft, according to one or more aspects of the present invention, may comprise gathering a plurality of empirical data sets, each data set corresponding to an individual golf shaft selected from a plurality of golf shafts; providing a plurality of specification codes, each associated with an individual empirical data set of the plurality of empirical data sets; from the plurality of specification codes, identifying a first specification code associated with the existing golf shaft; gathering feedback associated with the existing golf shaft from the player; and using the feedback to select, from the plurality of specification codes, a second specification code corresponding to the preferred golf shaft.

10 Claims, 8 Drawing Sheets

Related U.S. Application Data continuation of application No. 13/967,106, filed on Aug. 14, 2013, now Pat. No. 8,827,828, which is a continuation of application No. 13/681,544, filed on Nov. 20, 2012, now Pat. No. 8,535,174, which is a continuation of application No. 12/896,217, filed on Oct. 1, 2010, now Pat. No. 8,337,336.

(60) Provisional application No. 61/260,695, filed on Nov. 12, 2009.

(51) Int. Cl.

| | | |
|---|---|---|
| *A63B 53/00* | (2015.01) | |
| *G01N 19/00* | (2006.01) | |
| *G06F 17/00* | (2006.01) | |
| *A63B 53/04* | (2015.01) | |
| *A63B 71/06* | (2006.01) | |
| *A63B 60/00* | (2015.01) | |

(52) U.S. Cl.
CPC ............. *A63B 71/06* (2013.01); *G01N 19/00* (2013.01); *G06F 17/00* (2013.01); *A63B 2060/002* (2015.10); *A63B 2071/0694* (2013.01)

(58) Field of Classification Search
CPC .... A63B 2071/0694; A63B 2059/0003; A63B 2060/002; A63B 60/42; G01N 19/00; G06F 17/00

See application file for complete search history.

(56) References Cited

U.S. PATENT DOCUMENTS

| | | | |
|---|---|---|---|
| 5,379,641 | A | 1/1995 | Paasivaara et al. |
| 5,591,091 | A | 1/1997 | Hackman |
| 5,620,380 | A | 4/1997 | Tennent et al. |
| 6,110,056 | A | 8/2000 | Yamamoto |
| 6,213,888 | B1 * | 4/2001 | Kawaguchi ........ A63B 24/0003 473/223 |
| 6,546,802 | B2 | 4/2003 | Shiraishi et al. |
| 6,571,640 | B2 | 6/2003 | Harrison |
| 6,652,389 | B2 | 11/2003 | Hisamatsu et al. |
| 6,702,692 | B1 | 3/2004 | Smith |
| 6,719,648 | B1 | 4/2004 | Smith |
| 6,764,414 | B2 | 7/2004 | Kumamoto |
| 6,929,562 | B2 | 8/2005 | Kumamoto |
| 7,297,070 | B2 | 11/2007 | Ashida et al. |
| 7,300,358 | B2 | 11/2007 | Noble |
| 7,427,240 | B2 | 9/2008 | Takeuchi |
| 2002/0091009 | A1 | 7/2002 | Weiss et al. |
| 2006/0128494 | A1 | 6/2006 | Kumamoto |
| 2007/0113626 | A1 | 5/2007 | Silvey |
| 2007/0298902 | A1 | 12/2007 | Hasegawa |
| 2008/0305882 | A1 | 12/2008 | Noble et al. |
| 2009/0114034 | A1 | 5/2009 | Jertson |
| 2011/0275451 | A1 | 11/2011 | Chao et al. |

* cited by examiner

TABLE 1

R-Values for Pierce's Criterion

| Sample Size | \multicolumn{9}{c}{NUMBER OF DOUBTFUL OBSERVATIONS} | | | | | | | | |
|---|---|---|---|---|---|---|---|---|---|
| | 1 | 2 | 3 | 4 | 5 | 6 | 7 | 8 | 9 |
| 3 | 1.196 | | | | | | | | |
| 4 | 1.383 | 1.078 | | | | | | | |
| 5 | 1.509 | 1.200 | | | | | | | |
| 6 | 1.610 | 1.299 | 1.099 | | | | | | |
| 7 | 1.693 | 1.382 | 1.187 | 1.022 | | | | | |
| 8 | 1.763 | 1.453 | 1.261 | 1.109 | | | | | |
| 9 | 1.824 | 1.515 | 1.324 | 1.178 | 1.045 | | | | |
| 10 | 1.878 | 1.570 | 1.380 | 1.237 | 1.114 | | | | |
| 11 | 1.925 | 1.619 | 1.430 | 1.289 | 1.172 | 1.059 | | | |
| 12 | 1.969 | 1.663 | 1.475 | 1.336 | 1.221 | 1.118 | 1.009 | | |
| 13 | 2.007 | 1.704 | 1.516 | 1.379 | 1.266 | 1.167 | 1.070 | | |
| 14 | 2.043 | 1.741 | 1.554 | 1.417 | 1.307 | 1.210 | 1.120 | 1.026 | |
| 15 | 2.076 | 1.775 | 1.589 | 1.453 | 1.344 | 1.249 | 1.164 | 1.078 | |
| 16 | 2.106 | 1.807 | 1.622 | 1.486 | 1.378 | 1.285 | 1.202 | 1.122 | 1.039 |
| 17 | 2.134 | 1.836 | 1.652 | 1.517 | 1.409 | 1.318 | 1.237 | 1.161 | 1.084 |
| 18 | 2.161 | 1.864 | 1.680 | 1.546 | 1.438 | 1.348 | 1.268 | 1.195 | 1.123 |
| 19 | 2.185 | 1.890 | 1.707 | 1.573 | 1.466 | 1.377 | 1.298 | 1.226 | 1.158 |
| 20 | 2.209 | 1.914 | 1.732 | 1.599 | 1.492 | 1.404 | 1.326 | 1.255 | 1.190 |
| 21 | 2.230 | 1.938 | 1.756 | 1.623 | 1.517 | 1.429 | 1.352 | 1.282 | 1.218 |
| 22 | 2.251 | 1.960 | 1.779 | 1.646 | 1.540 | 1.452 | 1.376 | 1.308 | 1.245 |
| 23 | 2.271 | 1.981 | 1.800 | 1.668 | 1.563 | 1.475 | 1.399 | 1.332 | 1.270 |
| 24 | 2.290 | 2.000 | 1.821 | 1.689 | 1.584 | 1.497 | 1.421 | 1.354 | 1.293 |
| 25 | 2.307 | 2.019 | 1.840 | 1.709 | 1.604 | 1.517 | 1.442 | 1.375 | 1.315 |
| 26 | 2.324 | 2.037 | 1.859 | 1.728 | 1.624 | 1.537 | 1.462 | 1.396 | 1.336 |
| 27 | 2.341 | 2.055 | 1.877 | 1.746 | 1.642 | 1.556 | 1.481 | 1.415 | 1.356 |
| 28 | 2.356 | 2.071 | 1.894 | 1.764 | 1.660 | 1.574 | 1.500 | 1.434 | 1.375 |
| 29 | 2.371 | 2.088 | 1.911 | 1.781 | 1.677 | 1.591 | 1.517 | 1.452 | 1.393 |
| 30 | 2.385 | 2.103 | 1.927 | 1.797 | 1.694 | 1.608 | 1.534 | 1.469 | 1.411 |
| 31 | 2.399 | 2.118 | 1.942 | 1.812 | 1.710 | 1.624 | 1.550 | 1.486 | 1.428 |
| 32 | 2.412 | 2.132 | 1.957 | 1.828 | 1.725 | 1.640 | 1.567 | 1.502 | 1.444 |
| 33 | 2.425 | 2.146 | 1.971 | 1.842 | 1.740 | 1.655 | 1.582 | 1.517 | 1.459 |
| 34 | 2.438 | 2.159 | 1.985 | 1.856 | 1.754 | 1.669 | 1.597 | 1.532 | 1.475 |
| 35 | 2.450 | 2.172 | 1.998 | 1.870 | 1.768 | 1.683 | 1.611 | 1.547 | 1.489 |
| 36 | 2.461 | 2.184 | 2.011 | 1.883 | 1.782 | 1.697 | 1.624 | 1.561 | 1.504 |
| 37 | 2.472 | 2.196 | 2.024 | 1.896 | 1.795 | 1.711 | 1.638 | 1.574 | 1.517 |
| 38 | 2.483 | 2.208 | 2.036 | 1.909 | 1.807 | 1.723 | 1.651 | 1.587 | 1.531 |
| 39 | 2.494 | 2.219 | 2.047 | 1.921 | 1.820 | 1.736 | 1.664 | 1.600 | 1.544 |
| 40 | 2.504 | 2.230 | 2.059 | 1.932 | 1.832 | 1.748 | 1.676 | 1.613 | 1.556 |

FIG. 6A

| 41 | 2.514 | 2.241 | 2.070 | 1.944 | 1.843 | 1.760 | 1.688 | 1.625 | 1.568 |
| --- | --- | --- | --- | --- | --- | --- | --- | --- | --- |
| 42 | 2.524 | 2.251 | 2.081 | 1.955 | 1.855 | 1.771 | 1.699 | 1.636 | 1.580 |
| 43 | 2.533 | 2.261 | 2.092 | 1.966 | 1.866 | 1.783 | 1.711 | 1.648 | 1.592 |
| 44 | 2.542 | 2.271 | 2.102 | 1.976 | 1.876 | 1.794 | 1.722 | 1.659 | 1.603 |
| 45 | 2.551 | 2.281 | 2.112 | 1.997 | 1.897 | 1.815 | 1.743 | 1.681 | 1.625 |
| 46 | 2.560 | 2.290 | 2.122 | 1.997 | 1.897 | 1.815 | 1.743 | 1.681 | 1.625 |
| 47 | 2.568 | 2.299 | 2.131 | 2.006 | 1.907 | 1.825 | 1.754 | 1.691 | 1.636 |
| 48 | 2.577 | 2.308 | 2.140 | 2.016 | 1.917 | 1.835 | 1.764 | 1.701 | 1.646 |
| 49 | 2.585 | 2.317 | 2.149 | 2.026 | 1.927 | 1.844 | 1.773 | 1.711 | 1.656 |
| 50 | 2.592 | 2.326 | 2.158 | 2.035 | 1.936 | 1.854 | 1.783 | 1.721 | 1.666 |
| 51 | 2.600 | 2.334 | 2.167 | 2.044 | 1.945 | 1.863 | 1.792 | 1.730 | 1.675 |
| 52 | 2.608 | 2.342 | 2.175 | 2.052 | 1.954 | 1.872 | 1.802 | 1.740 | 1.685 |
| 53 | 2.615 | 2.350 | 2.184 | 2.061 | 1.963 | 1.881 | 1.811 | 1.749 | 1.694 |
| 54 | 2.622 | 2.358 | 2.192 | 2.069 | 1.972 | 1.890 | 1.820 | 1.758 | 1.703 |
| 55 | 2.629 | 2.365 | 2.200 | 2.077 | 1.980 | 1.898 | 1.828 | 1.767 | 1.711 |
| 56 | 2.636 | 2.373 | 2.207 | 2.085 | 1.988 | 1.907 | 1.837 | 1.775 | 1.720 |
| 57 | 2.643 | 2.380 | 2.215 | 2.093 | 1.996 | 1.915 | 1.845 | 1.784 | 1.729 |
| 58 | 2.650 | 2.387 | 2.223 | 2.101 | 2.004 | 1.923 | 1.853 | 1.792 | 1.737 |
| 59 | 2.656 | 2.394 | 2.230 | 2.109 | 2.012 | 1.931 | 1.861 | 1.800 | 1.745 |
| 60 | 2.663 | 2.401 | 2.237 | 2.116 | 2.019 | 1.939 | 1.869 | 1.808 | 1.753 |

SHAFT FITTING SYSTEM

This is a Continuation of application Ser. No. 14/449,906, filed Aug. 1, 2014, which is a Continuation of application Ser. No. 13/967,106, filed Aug. 14, 2013, which is a Continuation of application Ser. No. 13/681,544, filed Nov. 20, 2012, which is a Continuation of application Ser. No. 12/896,217 filed Oct. 1, 2010 (now U.S. Pat. No. 8,337,217 B2 issued Dec. 25, 2012), which claims the benefit of U.S. Provisional Application No. 61/260,695 filed Nov. 12, 2009. The disclosure of the prior applications is hereby incorporated by reference herein in its entirety.

COPYRIGHT AUTHORIZATION

The disclosure below may be subject to copyright protection. The copyright owner has no objection to the facsimile reproduction by anyone of the documents containing this disclosure, as they appear in the Patent and Trademark Office records, but otherwise reserves all applicable copyrights.

BACKGROUND

It is well known in the art of golf-club making that the accuracy, trajectory, and distance of a golf shot are influenced by the flex or stiffness of a golf shaft. The bending stiffness of a golf shaft is commonly represented in terms of a frequency, since bending stiffness and vibration frequency are interrelated. Most manufacturers clamp the shaft only at the butt end to measure the vibration frequency. However, vibration frequency measurements, performed in this manner, do not accurately represent the bending stiffness across the entire shaft. Alternatively, the bending stiffness of a golf shaft may be determined by measuring the cantilever displacement of the golf shaft under a known load. These measurements are typically taken only at the butt and tip sections of the shaft, thus providing limited bending stiffness data to the golfer.

Additionally, the torsional stiffness of a golf shaft may be determined by measuring the torsional displacement of the shaft under an applied torque for a given cantilever length. This method generates an overall torsional stiffness value for the shaft, but does not provide the varying localized torsional stiffness values across the shaft. Accordingly, it is difficult to tine tune the torsional stiffness of the shaft to fit the needs of the player.

SUMMARY

The present invention, in one or more aspects thereof, may comprise an advantageous method of selecting a golf shaft that provides improved player performance.

In one example, a method of selecting a preferred golf shaft for a player who uses an existing golf shaft, according to one or more aspects of the present invention, may comprise gathering a plurality of empirical data sets, each data set corresponding to an individual golf shaft selected from a plurality of golf shafts; providing a plurality of specification codes, each associated with an individual empirical data set of the plurality of empirical data sets; from the plurality of specification codes, identifying a first specification code associated with the existing golf shaft; gathering feedback associated with the existing golf shaft from the player; and using the feedback to select, from the plurality of specification codes, a second specification code corresponding to the preferred golf shaft.

In another example, a method of selecting a preferred golf shaft for a player who uses an existing golf shaft, according to one or more aspects of the present invention, may comprise generating a plurality of bending stiffness profiles, each bending stiffness profile corresponding to an individual golf shaft selected from a plurality of golf shafts; providing a plurality of specification codes, each associated with an individual bending stiffness profile of the plurality of bending stiffness profiles; from the plurality of specification codes, identifying a first specification code corresponding to the existing golf shaft; gathering feedback associated with the existing golf shaft from the player; and using the feedback to select, from the plurality of specification codes, a second specification code corresponding to the preferred golf shaft.

In yet another example, a method of selecting a preferred golf shaft for a player who uses an existing golf shaft, according to one or more aspects of the present invention, may comprise generating a plurality of torsional stiffness profiles, each bending stiffness profile corresponding to an individual golf shaft selected from a plurality of golf shafts; providing a plurality of specification codes, each associated with an individual bending stiffness profile of the plurality of torsional stiffness profiles; from the plurality of specification codes, identifying a first specification code corresponding to the existing golf shaft; gathering feedback associated with the existing golf shaft from the player; and using the feedback to select, from the plurality of specification codes, a second specification code corresponding to the preferred golf shaft.

In yet another example, a method of selecting a preferred golf shaft for a player who uses an existing golf shaft, according to one or more aspects of the present invention, may comprise gathering a plurality of empirical data sets, each data set corresponding to an individual golf shaft selected from a plurality of golf shafts; providing a plurality of specification codes, each associated with an individual empirical data set of the plurality of empirical data sets; from the plurality of specification codes, identifying a first specification code corresponding to the existing golf shaft; gathering feedback associated with the existing golf shaft from the player; using the feedback to select, from the plurality of specification codes, a second specification code corresponding to the preferred golf shaft; and substituting the existing golf shaft of the golf club with the preferred golf shaft.

In yet another example, a method of selecting a preferred golf shaft for a player who uses an existing golf shaft, according to one or more aspects of the present invention, may comprise gathering a plurality of empirical data sets, each data set corresponding to an individual golf shaft selected from a plurality of golf shafts; storing the plurality of empirical data sets in an electronic look-up table; performing a computational analysis to standardize the empirical data for the plurality of golf shafts to produce a corresponding plurality of specification codes; from the plurality of specification codes, identifying a first specification code corresponding to the existing golf shaft; gathering feedback associated with an existing golf shaft from the player; and using the feedback to select, from the plurality of specification codes, a second specification code corresponding to the preferred golf shaft.

These and other features and advantages of the fitting method according to the invention in its various aspects, as provided by one or more of the examples described in detail below, will become apparent after consideration of the ensuing description, the accompanying drawings, and the appended claims. The accompanying drawings are for illustrative purposes only and are not intended to limit the scope of the present invention.

BRIEF DESCRIPTION OF THE DRAWINGS

Exemplary implementations of the present invention will now be described with reference to the accompanying drawings, wherein:

FIGS. 6A and 6B illustrate a Pierce's Criterion R-value table.

DESCRIPTION

Figure 1:
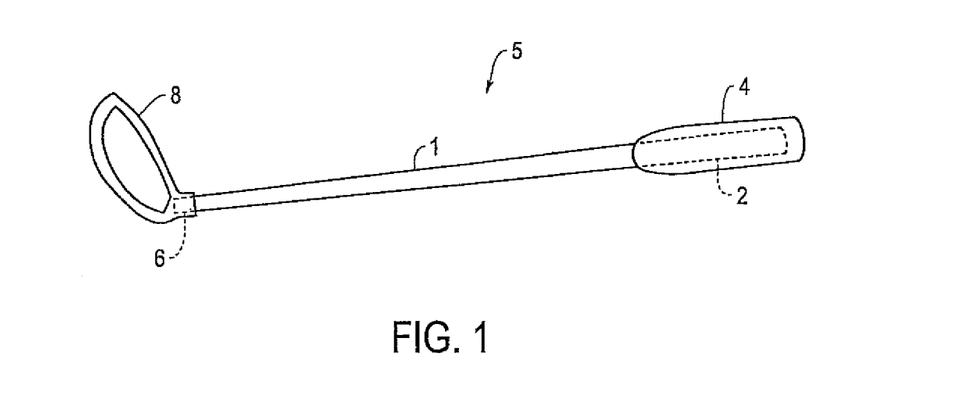
FIG. 1 is a perspective view of an exemplary golf club.

In accordance with one or more aspects of the present invention, a preferred golf shaft may be selected for a player, who uses an existing golf shaft, from a registry of commercially available golf shafts. As shown in FIG. 1, each golf shaft 1 may include a butt end 2, generally associated with a grip 4 of a golf club 5, and a tip end 6, generally associated with a head 8 of a golf club 5. Moreover, each golf shaft may be associated with a specification code, representative of a set of empirical data relating to, e.g., a stiffness profile of the golf shaft or a frequency profile of the golf shaft. The specification code may be indicated by any type of indicating medium such as a color, mark, numeric, alphabetical, or alphanumeric indicia.

Figure 2:
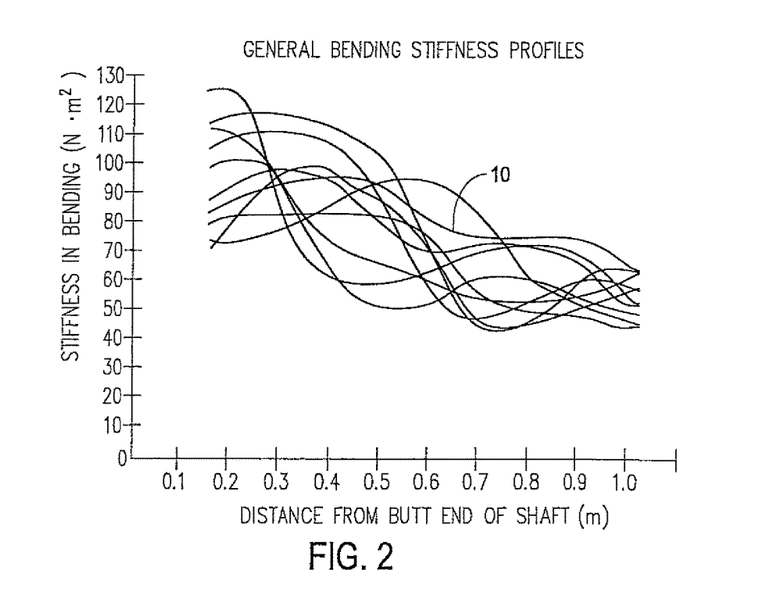
FIG. 2 is a plot of a plurality of shaft bending stiffness profiles.
Figure 3:
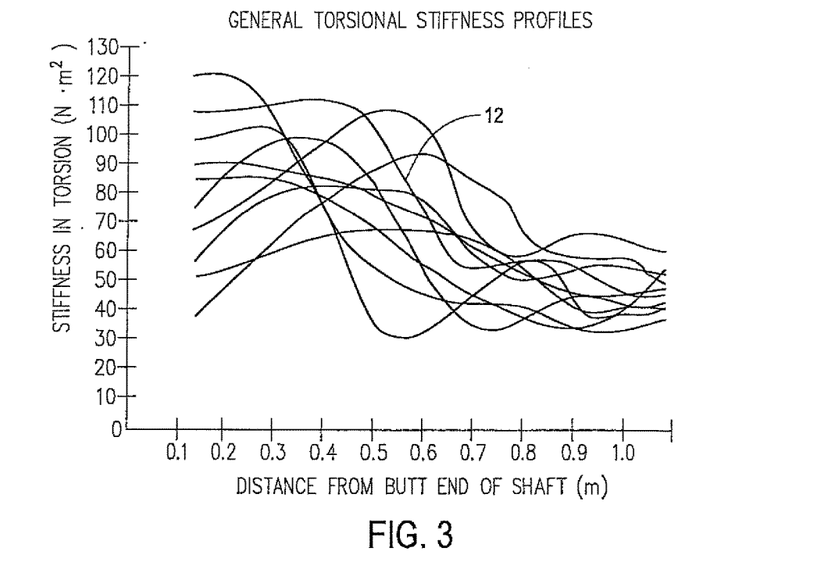
FIG. 3 is a plot of a plurality of shaft torsional stiffness profiles.

Manufacturers generally divide shafts into one of the following five stiffness categories: senior flex (A-flex); regular flex (R-flex); stiff flex (S-flex); extra stiff flex (X-flex); or double extra stiff flex (XX-flex). Referring to FIGS. 2 and 3, the stiffness profile for each shaft may be generated by measuring, e.g., the local stiffness in bending (FIG. 2) or the local stiffness in torsion (FIG. 3) at a plurality of points along the shaft. The localized stiffness in bending (EI) is defined as the product of the Young's modulus (E) and the moment of inertia (I) of the localized cross-sectional area of the shaft. Preferably, the bending stiffness profile, e.g., the bending stiffness profile 10, of each shaft is measured using, e.g., an automated EI curve tracer. The localized stiffness in torsion (GJ) is defined as the product of the Shear Modulus (G) and the polar moment of inertia (J). The torsional stiffness profile, e.g., the torsional stiffness profile 12, may be measured using, e.g., an automated GJ curve tracer.

Figure 4:
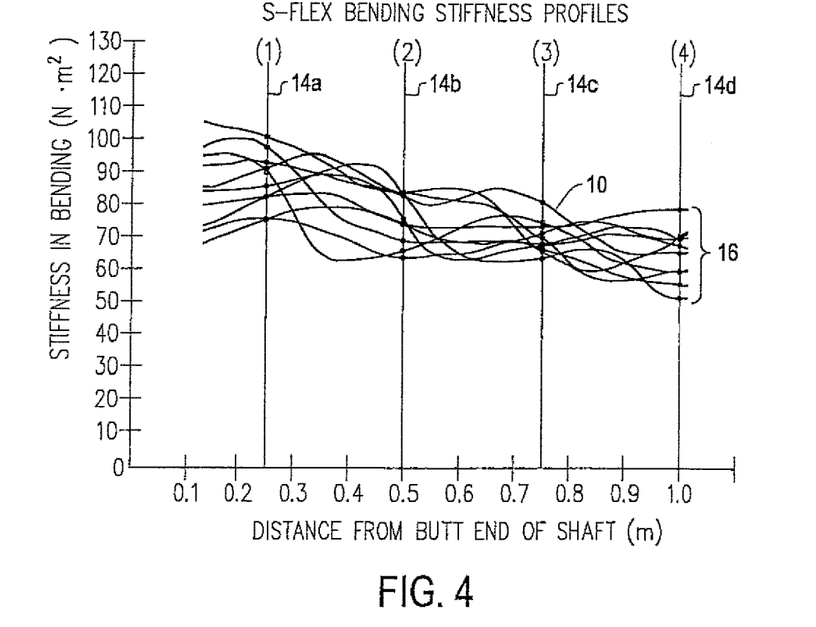
FIG. 4 is a plot of bending stiffness profiles for a plurality of S-flex shafts.
Figure 5:
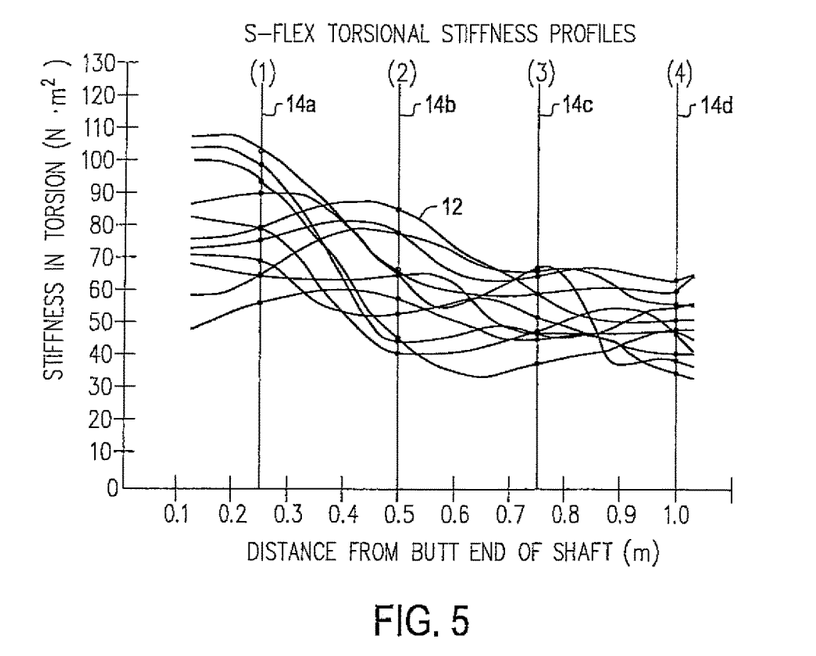
FIG. 5 is a plot of bending stiffness profiles for a plurality of S-flex shafts.

The stiffness profiles of each golf shaft may be converted into the appropriate specification code by using a formatting procedure. Initially, the stiffness profiles for all S-flex shafts are plotted on an x,y-coordinate plane wherein the x-axis represents the distance of the stiffness measurement from the butt end of the shaft and the y-axis represents the stiffness. Preferably, each of at least three vertical lines passes through a distinct point on the x-axis. For example, as shown in FIGS. 4 and 5, a first vertical line 14a may pass through a first x-value (1), e.g., 0.25 m, which represents a point proximate the butt end of the golf shaft, a second vertical line 14b may pass through a second x-value (2), e.g., 0.50 m, a third vertical line 14c may pass through a third x-value (3), e.g., 0.75 m, and a fourth vertical line 14d may pass through a fourth x-value (4), e.g., 1.00 m, which represents a point proximate the tip end of the golf shaft. For each x-value (1), (2), (3), and (4), the intersection of the vertical line with each S-flex stiffness profile delimits a set of S-flex data points, e.g., S-flex data set 16, wherein each data point has a corresponding y-value. Each S-flex data set may include one or more outliers, i.e., one or more S-flex data points that markedly deviate from other members of the S-flex data set. To eliminate the statistical outliers in each S-flex data set, a percentage of the data points, e.g., 0.5%, 1%, 2%, or 5% of the data points, having the highest and lowest y-values, may be eliminated from consideration. Alternatively, Pierce's Criterion may be applied to each S-flex data set to determine the statistically relevant measurements.

Figure 6B:
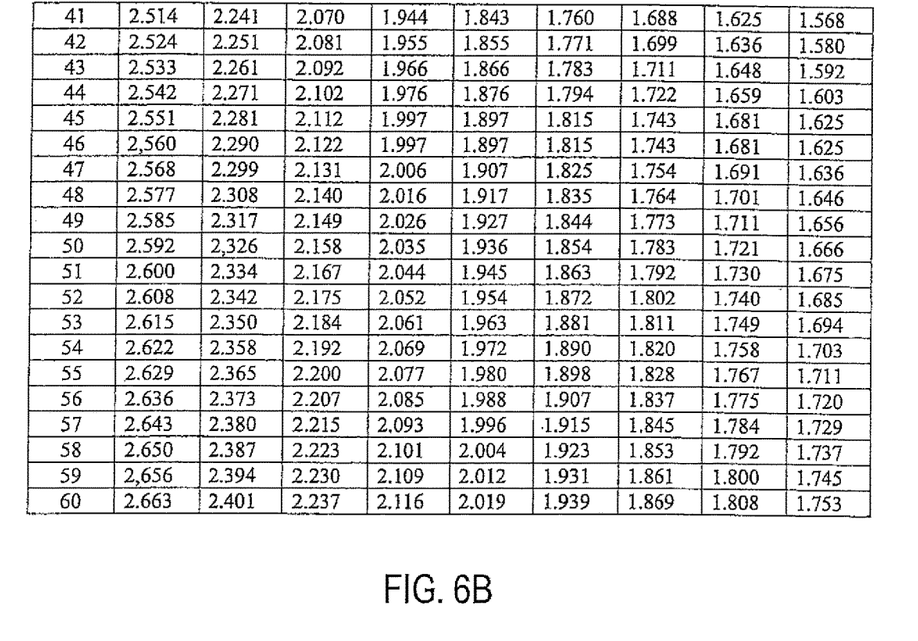

According to Pierce's Method, a measurement is considered a statistical outlier if the following relationship is satisfied:

$$|x_i - x_m| > \sigma R,$$

where $x_i$ is one of the measured data points in the S-flex data set, $x_m$ is the mean of the S-flex data set, $\sigma$ is the standard deviation of the S-flex data set, and R is the ratio of the maximum allowable deviation of an S-flex data point ($x_i$) from the mean ($x_m$) to the standard deviation ($\sigma$). As shown in FIGS. 6A and 6B, the appropriate R value depends on the sample size of an S-flex data set and the number of suspected outliers or "doubtful observations" to be rejected. Initially, it is assumed that one doubtful observation exists for an S-flex data set. After selecting the appropriate R value for one doubtful observation, each data point of an S-flex data set is tested for statistical relevance using Pierce's relationship, described above. If one data point of an S-flex data set is rejected, it is then assumed that two doubtful observations exist in the data set. However, if more than one data point of an S-flex data set is rejected for one doubtful observation, the next highest value of doubtful observations is selected. When testing each data point of an S-flex data set for statistical relevance, assuming two or more doubtful observations, the mean, the standard deviation, and the sample size retain the same values. After selecting the appropriate R value for two or more doubtful observations, the outliers are determined and eliminated using Pierce's relationship. The remaining outliers are eliminated by sequentially increasing the number of doubtful observations and following the same procedures, described above.

Figure 7:
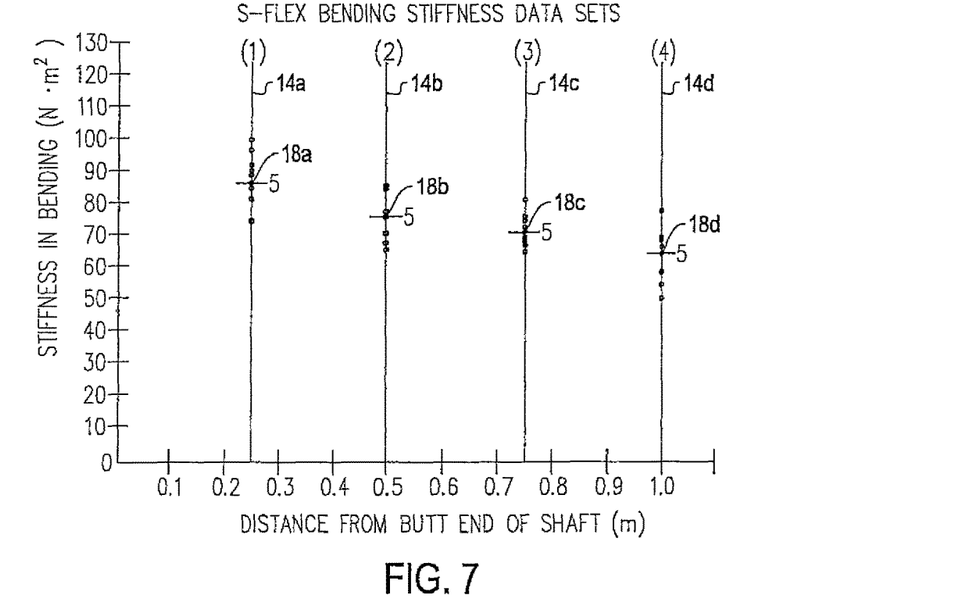
FIG. 7 is a plot of bending stiffness data sets for a plurality of S-flex shafts, according to one or more aspects of the present invention.
Figure 8:
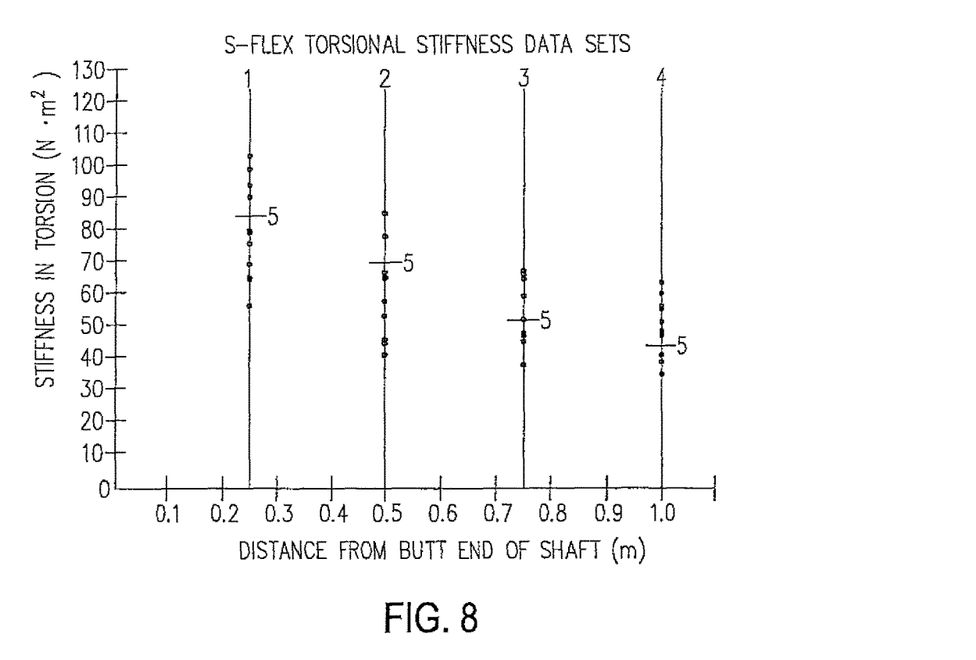
FIG. 8 is a plot of torsional stiffness data sets for a plurality of S-flex shafts, according to one or more aspects of the present invention.

Once the outliers have been eliminated, the mean or average y-value is identified for each S-flex data set at x-values (1), (2), (3), and (4). As shown in FIGS. 7 and 8, the average y-value, e.g., the average y-values 18a-d, for each S-flex data set may be designated with, e.g., the numeric code 5, on the x,y-coordinate plane. Separate stiffness plots may be generated for each remaining stiffness category, i.e., A-flex, R-flex, X-flex, and XX-flex. For each stiffness plot, a data set may be generated at each x-value (1), (2), (3), and (4) using the procedure, described above, for determining the S-flex data sets. The outliers for each data set may be eliminated by using Pierce's Criterion or by eliminating a percentage of data points, also discussed above. After all outliers are eliminated for each stiffness plot, the remaining data points of each data set are graphically aggregated on the S-flex stiffness plot.

Figure 9:
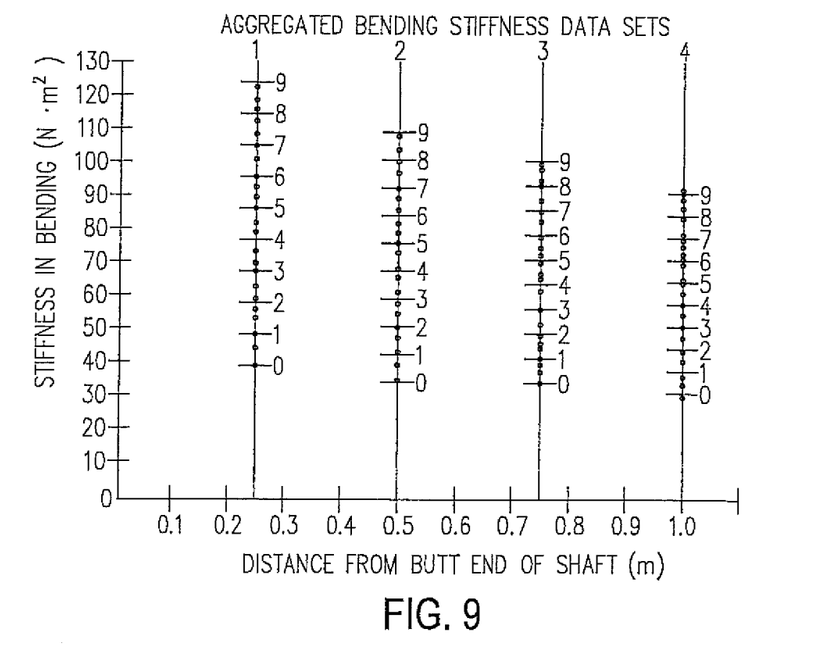
FIG. 9 is a plot of bending stiffness data sets for a plurality of shafts, with each data set being vertically graduated into ten equal increments.
Figure 10:
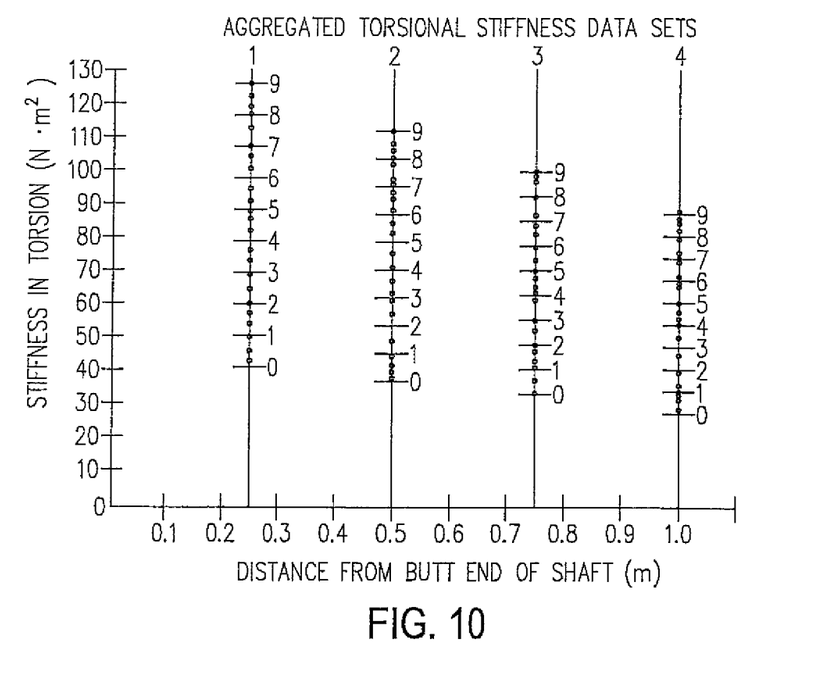
FIG. 10 is a plot of bending stiffness data sets for a plurality of shafts, with each data set being vertically graduated into ten equal increments.
Figure 11:
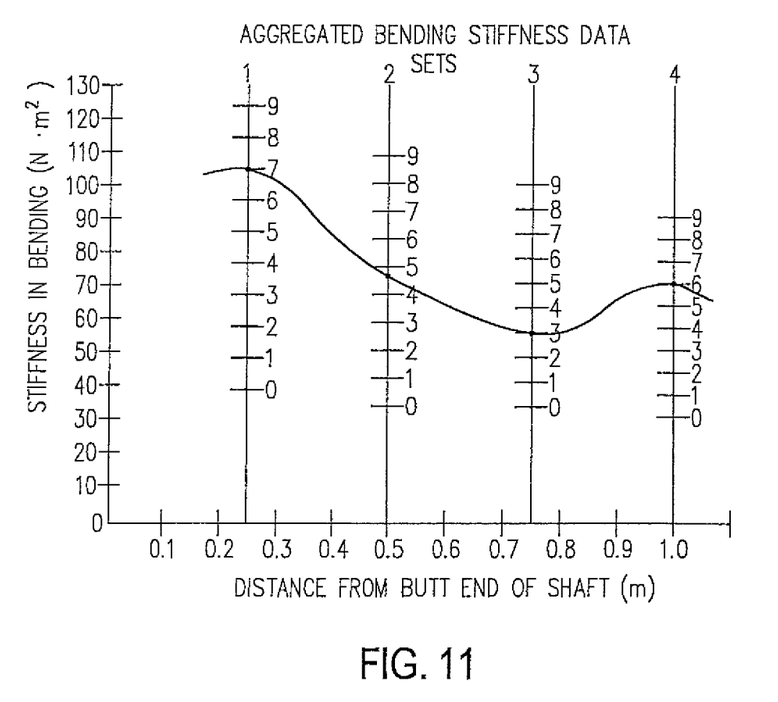
FIG. 11 is a plot of a bending stiffness profile for an exemplary shaft, according to one or more aspects of the present invention.

As shown in FIGS. 9 and 10, the plot containing the data points from all 5 stiffness categories is vertically graduated into ten equal increments, each labeled with, e.g., a distinct numeric code that sequentially increases from 0 to 9, at each x-value (1), (2), (3), and (4). The numeric code 0 substantially corresponds to the data point having the lowest overall y-value in the aggregated data set, and the numeric code 9 substantially corresponds to the data point having the greatest overall y-value in the aggregated data set. As described above, the numeric code 5 corresponds to the average y-value for the S-flex data set. Preferably, the numeric code 1 represents a stiffness generally corresponding to that of an A-flex shaft, the numeric code 3 represents a stiffness generally corresponding to that of an R-flex shaft, the numeric code 5 represents a stiffness generally corresponding to that of an S-flex shaft, the numeric code 7 represents a stiffness generally corresponding to that of an X-flex shaft, and the numeric code 9 represents a stiffness generally corresponding to that of a XX-flex shaft. Accordingly, each shaft may be converted into, e.g., a four digit numerical code, representative of the shafts relative stiffness (y-axis) at x-values (1), (2), (3), and (4) on the x,y-coordinate plane. For example, a golf shaft having the stiffness profile shown in FIG. 11 would have a specification code of 7536. Although the data point located at x-value (2) lies between the numeric codes 4 and 5, it is rounded to the nearest whole integer of the code set to preserve simplicity. Preferably, each stiffness profile is analyzed by a computer software program, which converts each stiffness profile into a specification code by automatically performing the code generating steps, described above. The specification code for each golf shaft model may be stored in a shaft registry, e.g., a printed chart or an electronic look-up table, and may be provided on the shaft.

Using the shaft registry, the specification code for the player's current shaft model may be identified. Preferably, the specification code corresponding to the player's current shaft is used as a threshold value in the process of selecting a preferred shaft having a new code associated therewith. To identify the new code, the threshold value may be modified based on player feedback relating to his or her current shaft's feel and performance. Player feedback may be gathered through a general feedback inquiry, e.g., an interview, a printed questionnaire, or an electronic interface. During the feedback inquiry, the player may provide general information about his or her current shot tendencies, e.g., average driver shot distance, swing speed, swing tempo, shot shape, and vertical ball flight/trajectory. A code adjustment value (CAV) may be assigned to each feedback response. For example, the player's average driver shot distance may be assigned one of a plurality of available code adjustment values, each representative of a particular distance range. More specifically, the player may be assigned one of the following four code adjustment values depending on how far he or she drives the ball: CAV 1111=<210 yards; CAV 3333=210 yards-240 yards; CAV 5555=240 yards-270 yards; and CAV 7777=>270 yards.

The integers of each code adjustment value may be averaged together to generate an average code adjustment value. If, for example, the code adjustment value is identified as 5555, the average code adjustment value would be 5, i.e., (5+5+5+5)/4. A similar method may be utilized to generate an average threshold value. For example, if the threshold value is 8866, the average threshold value would be 7, i.e., (8+8+6+6)/4. Accordingly, each integer of a threshold value may be decreased by the difference between the average threshold value and the average code adjustment value. Thus, if the average threshold value is 7 and the average code adjustment value is 5, each integer of a threshold value, e.g., 8866, would be decreased by a value of 2 for a final value of, e.g., 6644. Once the threshold value has been modified, the new value may represent either the new code or an intermediate value that may be further modified.

Alternatively, the player's average swing speed, rather than the average driver shot distance, may be assigned one of a plurality of available code adjustment values, each representative of a particular swing speed range. More specifically, the player may be assigned one of the following four code adjustment values depending on how fast he or she can swing the club head: CAV 1111=<85 m.p.h.; CAV 3333=85 m.p.h.-100 m.p.h.; CAV 5555=100 m.p.h.-115 m.p.h.; and CAV 7777=>115 m.p.h. As described above, each integer of a threshold value may be decreased by the difference between the average threshold value and the average code adjustment value. Once the threshold value has been modified, the new value may represent either the new code or an intermediate value that may be further modified.

In another example, according to one or more aspects of the present invention, one or more integers of a threshold value (or an intermediate value, described above) may be modified based on the player's swing tempo. If, for example, the player's swing tempo comprises a substantially constant angular acceleration, one or more integers of the threshold value (or the intermediate value) may be increased by a value between, e.g., about 1 and about 1.5. Alternatively, if the player's swing tempo comprises a variable angular acceleration, one or more integers of the threshold value (or intermediate value) may be decreased by a value between, e.g., about 1 and about 1.5. Once the threshold value (or the intermediate value) has been modified, the new value may represent either the new code or an intermediate value that may be further modified.

In yet another example, according to one or more aspects of the present invention, one or more integers of a threshold value (or an intermediate value, described above) may be modified based on the player's desired shot shape. If, for example, the player wants his or her shot to draw, the average threshold value (or the average intermediate value) may be reduced by a value between, e.g., about 1 and about 2. Alternatively or additionally, the first integer of the threshold value (or the intermediate value) may be increased by a value between, e.g., about 1 and about 2, and the final integer of the threshold value (or the intermediate value) may be decreased by a value between, e.g., about 1 and about 2. If, instead, the player wants his or her shot to fade, the average threshold value (or the average intermediate value) may be increased by a value between, e.g., about 1 and about 2. Alternatively or additionally, the first integer of the threshold value (or the intermediate value) may be decreased by a value between, e.g., about 1 and about 2, and the final integer of the threshold value (or the intermediate value) may be increased by a value between, e.g., about 1 and about 2. Once the threshold value (or the intermediate value) has been modified, the new value may represent either the new code or an intermediate value that may be further modified.

In yet another example, according to one or more aspects of the present invention, one or more integers of a threshold value (or an intermediate value, described above) may be modified based on the vertical ball flight and/or the trajectory of a player's shot. If, for example, the vertical ball flight, the launch angle, and/or the spin rate of the golf ball are too high, the first integer of the threshold value (or the intermediate value) may be increased by a maximum value of, e.g., about 2. If, however, the vertical ball flight, the launch angle, and/or the spin rate of the golf ball are too low, the last integer of the threshold value (or the intermediate value) may be decreased by a maximum value of, e.g., about 2. Once the threshold value (or intermediate value) has been modified, the new value may represent either the new code or an intermediate value that may be further modified.

In yet another example, according to one or more aspects of the present invention, one or more integers of a threshold value (or an intermediate value) may be modified based on player feedback relating to the feel of the shaft during a golf swing. Accordingly, if the player describes the overall stiffness of the shaft as too stiff, the average threshold value (or the average intermediate value) is decreased. Alternatively, if the player describes the overall stiffness of the shaft as too flexible, the average threshold value (or the average intermediate value) is decreased. Once the threshold value or intermediate value has been modified, the new value may represent either the new code or an intermediate value that may be further modified.

After the new specification code is identified using player feedback, the player's current shaft may, e.g., be substituted with a preferred shaft having the new specification code associated therewith. In some instances, the player's current shaft may be strategically cut at the tip and/or the butt such that the player's current shaft is converted into the preferred shaft having the new specification code associated therewith. The preferred shaft may be fabricated or ordered from an established supplier.

In the foregoing specification, the invention has been described with reference to specific exemplary aspects thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A golf shaft selection method, comprising:
accessing a plurality of specification codes, wherein each specification code uniquely indicates a stiffness profile including a first, second, and third normalized value corresponding to actual stiffness values at respective first, second, and third longitudinal positions about a golf shaft, the normalized values being normalized based on predetermined stiffness scales;
for each of a plurality of golf club shafts having unique stiffness profiles, uniquely assigning a specification code of the plurality of specification codes by correlating stiffness properties of the particular shaft with one of the stiffness profiles represented by the plurality of unique specification codes;
receiving swing feedback from a player, the swing feedback including at least one of: average driver shot distance, swing speed, shot shape, and vertical ball trajectory;
correlating the swing feedback with a recommended specification code of the plurality of specification codes according to a predetermined relationship between swing feedback and the plurality of unique specification codes;
locating the specification code on each of the plurality of shafts in the form of indicia; and
outputting, based on the recommended specification code, a shaft from the plurality of shafts.

2. The method of claim 1, wherein each of the first, second, and third normalized values are unitless.

3. The method of claim 2, wherein each of the first, second, and third normalized values is an integer within a range of zero to nine.

4. The method of claim 3, wherein the range of integers corresponds to a range of stiffness such that a higher integer represents a higher stiffness.

5. The method of claim 1, wherein the first, second, and third normalized values are ordered such that the first longitudinal position is a location closest to the butt end of the shaft and the second and third longitudinal positions are each at a respective location increasingly further away from butt end of the shaft.

6. A golf shaft selection method, comprising:
accessing a plurality of specification codes, wherein each specification code uniquely indicates a stiffness profile including a first, second, and third normalized value corresponding to actual stiffness values at respective first, second, and third longitudinal positions about a golf shaft, the normalized values being normalized based on predetermined stiffness scales;
for each of a plurality of golf club shafts having unique stiffness profiles, uniquely assigning a specification code of the plurality of specification codes by correlating stiffness properties of the particular shaft with one of the stiffness profiles represented by the plurality of unique specification codes;
receiving swing feedback from a player, the swing feedback including at least one of: average driver shot distance, swing speed, shot shape, and vertical ball trajectory;
correlating the swing feedback with a recommended specification code according to a predetermined relationship between swing feedback and the plurality of unique specification codes;
locating the specification code on each of the plurality of shafts in the form of indicia; and
outputting, based on the recommended specification code, a shaft from the plurality of shafts.

7. The method of claim 6, wherein the first, second, and third normalized values are unitless.

8. The method of claim 7, wherein each of the first, second, and third normalized values is an integer within a range of zero to nine.

9. The method of claim 8, wherein the range of integers corresponds to a range of stiffness such that a higher integer represents a higher stiffness.

10. The method of claim 6, wherein the first, second, and third normalized values are ordered such that the first longitudinal position is a location closest to the butt end of the shaft and the second and third longitudinal positions are each at a respective location increasingly further away from butt end of the shaft.

\* \* \* \* \*